United States Patent [19]

Carey et al.

[11] Patent Number: 4,548,922

[45] Date of Patent: Oct. 22, 1985

[54] DRUG ADMINISTRATION

[75] Inventors: Martin C. Carey, Wellesley; Alan C. Moses, Waban; Jeffrey S. Flier, Newton, all of Mass.

[73] Assignees: Beth Israel Hospital; The Brigham & Women's Hospital, Inc., both of Boston, Mass.

[21] Appl. No.: 501,187

[22] Filed: Jun. 6, 1983

[51] Int. Cl.$^4$ ...................... A61K 37/26; A61K 31/56
[52] U.S. Cl. .......................................... 514/4; 514/171
[58] Field of Search .................. 424/178, 240, 243; 514/4, 171

[56] References Cited

U.S. PATENT DOCUMENTS

| | | | |
|---|---|---|---|
| 3,867,413 | 2/1975 | Von Daehne et al. | 260/397.1 |
| 4,060,606 | 11/1977 | Daehne et al. | 424/243 |
| 4,100,276 | 7/1978 | Daehne et al. | 424/243 |
| 4,119,717 | 10/1978 | Daehne et al. | 424/243 |
| 4,153,689 | 5/1979 | Hirai et al. | 260/397.1 |
| 4,501,734 | 2/1985 | Tanaka et al. | 514/198 |

FOREIGN PATENT DOCUMENTS 1527605  10/1978  United Kingdom ................ 424/243

OTHER PUBLICATIONS

S. Hirai et al., *Diabetes,* 27(3):296–299, (Mar. 1978).
S. Hirai et al., *Int. J. Pharmaceutics,* 9:165–172, 9:173–184, (1981).
A. E. Pontiroli et al., *British Medical Journal,* 284:303–306, (1982).
M. J. Armstrong and M. C. Carey, *J. Lipid Res.,* 23(1):70–80, (1982).

*Primary Examiner*—Elbert L. Roberts
*Attorney, Agent, or Firm*—Pennie & Edmonds

[57] ABSTRACT

A composition useful for the treatment of an animal suffering from a predetermined medical disorder including, in admixture, a medically effective amount of a drug, other than an antibiotic, effective against the medical disorder, and a biocompatible, water-soluble, amphiphilic steroid, other than a bile salt, which is capable of increasing the permeability to the drug of a surface of the animal across which the drug is to be administered, in an amount effective to increase the permeability of the surface to the drug.

33 Claims, No Drawings

DRUG ADMINISTRATION

BACKGROUND OF THE INVENTION

This invention was supported in part by a grant or award from the United States Government, which has rights in the invention.

This invention relates to the administration of drugs across animal body surfaces. (As used herein, "drug" means any chemical substance other than an antibiotic useful for treating a medical disorder of an animal).

Certain drugs, e.g. insulin, which need to be administered frequently are not effectively absorbed when administered orally. For example, a number of problems are associated with conventional insulin therapy. Because of the necessity for and discomfort associated with frequent insulin injections, the patient's lifestyle is disrupted. Hence, many diabetics either refuse insulin therapy altogether or avoid intensive treatment regimes such as those which involve injections with each meal. In addition, certain patients, especially young children, elderly patients, and those who are blind and/or disabled, are precluded from insulin self-administration by injection. Furthermore, insulin absorption after subcutaneous injection is variable in terms of rate and amount depending upon factors such as exercise, local blood flow, depth and volume of injection, the presence of local proteases which degrade insulin, and perhaps other, unknown factors. Portable infusion pumps have now been employed to increase the ease of delivering subcutaneously meal-related insulin boluses. However, these devices are externally worn and therefore cumbersome, they require regular needle replacement, are expensive, and are not accepted by many patients. It is clear that a reproducible, reliable, and non-invasive means for delivering insulin would be highly desirable. What is needed especially is an insulin delivery system that would permit easy, rapid, and non-invasive administration of insulin at meal times, when blood glucose concentration rises to peak levels.

Since the discovery of insulin six decades ago, there have been many attempts to develop alternate means of insulin delivery. Insulin has been administered enterally, either alone or encapsulated in liposomes (microcapsules); sublingually; vaginally; reactally with or without surfactants; and as a nasal aerosol spray.

It is well known that certain small peptides can be absorbed through the nasal mucosa as a "snuff" or directly from aqueous solution without an adjuvant. Examples of peptides which can be administered by this route are vasopressin, adrenocorticotrophic hormone (ACTH), luteinizing hormone relasing hormone (LHRH), and oxytocin. Indeed, for patients with diabetes insipidus, the intranasal route is a standard means for vasopressin delivery. In contrast, in the absence of adjuvants, insulin, and many other drugs, are not absorbed across the nasal mucosa at physiological pH.

Several workers have attempted to mix insulin with adjuvants that might enhance nasal insulin absorption. Hirai et al. (*Int. J. Pharmaceutics* (1981) 9 165–184; *Diabetes* (1978) 27, 296–299; British Pat. No. 1,527,605; and U.S. Pat. No. 4,153,689; and Pontiroli et al. (1982) *Br. Med J.* 284, 303–386, have described the use of various bile salts to enhance absorption of insulin by the nasal mucosa.

SUMMARY OF THE INVENTION

We have discovered an effective means of administering a drug to an animal which avoids many of the problems associated with other modes of adminstration such as injection. The invention features, in one aspect, a composition useful for the treatment of an animal suffering fromm a predetermined medical disorder including, in admixture, a medically effective amount of a drug, other than an antibiotic, effective against the medical disorder, and a biocompatible, water-soluble, amphiphilic steroid, other than a bile salt, which is capable of increasing the permeability to the drug of a surface of the animal across which the drug is to be administered, in an amount effective to increase the permeability of the surface to the drug.

Preferably the steroid is one of the naturally occurring steroids, fusidic acid or cephalosporin $P_1$, or a derivative of either of these. Preferably the steroid has the following formula:

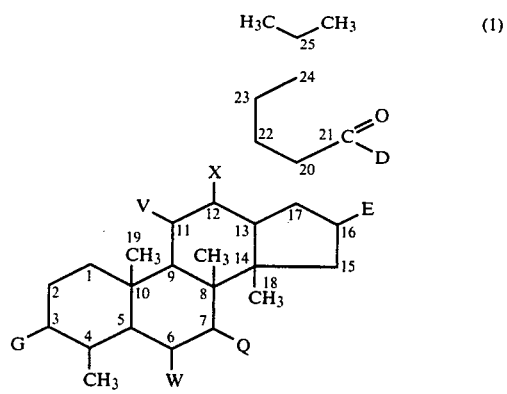

wherein each dashed line, independently, represents a single or a double bond; D is a group which renders an effective amount of the steroid water soluble at pH 7.4; E is OAc or a lower (3 or fewer carbons) alkyl or heteroalkyl group; G is OAc, OH, lower alkyl, or lower heteroalkyl; W is OAc or H; Q is OH or H, provided that, when W is OAc and Q is OH, Q must be β-equatorial; V is H or α-axial OH; and X is H or α-axial OH; provided that the steroid contains between 0 and two OH groups, inclusive (Ac refers to the acyl radical $OCOCH_3$).

The steroid of formula (1) can be unconjugated, i.e. D is $O^-Na^+$, $O^-K^+$, $O^-Rb^+$, $O^-Cs^{30}$, or some other ionic configuration, or it can be conjugated, i.e. D is an organic group containing at least two carbon atoms. Preferably group D has a molecular weight below 600 daltons and is one of the following groups:

(A) a peptide of one, two, or three amino acids and containing an ionic function which is dissociated at pH 7.4;

(B) a heteroalkyl group of three or fewer carbon atoms which contains an ionic function which is dissociated at pH 7.4;

(C) A uronic acid of six or fewer carbon atoms which contains an ionic function which is dissociated at pH 7.4;

(D) a polyether containing between six and fourteen carbon atoms, inclusive, which terminates in an ionic function which is dissociated at pH 7.4; or (E) a polyether containing between sixteen and twenty-four carbon atoms, inclusive, and optionally terminating in an ionic function which is dissociated at pH 7.4.

Group D is preferably bonded to $C_{21}$ via an amide or ester linkage.

Preferably the steroid used in the invention is characterized in that the unconjugated derivative of the steroid is retained on a hydrophobic column for a length of time sufficient to produce a k' factor value of at least 7, the k' factor value being obtained by subjecting a monomeric solution of 1 mg/ml of such steroid derivative to high-performance liquid column chromatography at 3,000 psi, using a 250×4.6 mm column having octadecylsilane-coated 5 μm micro silica particles as the stationary phase and a mobile phase, delivered at 1.0 ml/min., consisting of 75% methanol in water, v/v, buffered with 0.005 M $KH_2PO_4/H_3PO_4$ to give an apparent pH value, as measured using a glass electrode, of 5.0, the k' factor value being defined by $k' = (t_r - t_0)/t_0$, where $t_0$ is the retention time in the column of the solvent front and $t_r$ is the retention time in the column of the steroid derivative as measured by obtaining the elution profile of the steroid derivative by absorbance at 210 nm.

Preferably the steroid is further characterized in that the critical micellar temperature (the temperature at which the steriod ceases to be an insoluble crystal or gel and begins to self-associate in solution) of an aqueous 1% solution, w/v, of the steroid is below 4° C. at pH 7.4 (a measure of solubility); and the critical micellar concentration (CMC) (the concentration at which the steroid ceases to form an ideal solution and begins to self-associate) is less than 4 mMolar at 37° C. in 0.15 M NaCl as measured by surface tension.

Preferred steroids are fusidic acid; 24, 25 dihydrofusidic acid, 17-20, 24-25 tetrahydrofusidic acid; 3-acetoxyl-fusidic acid; cephalosporin $P_1$; and $C_{21}$ conjugates of these. Preferably the drug to be administered is a peptide which has a molecular weight between about 100 and about 40,000 daltons; preferably the drug is a hormone, most preferably insulin.

The invention permits the administration across a surface of an animal, e.g. epithelial surfaces such as the nasal mucosa, of drugs which normally cannot be so administered. Administration, according to the invention, is associated with minimal toxic side effects because the steroid molecules admixed with the drug have low local toxicity. Thus the steroids of the invention are able to potentiate the transport of drugs across mucosal membranes into the circulation while causing little or no burning sensation which is a characteristic by-product of transport facilitation by other carrier molecules.

The invention allows drug administration to be tailored much more closely to cyclic disease states than is possible with other forms of administration. This is of particular importance with diseases such as diabetes, in which insulin requirements vary during the course of a day.

Other features and advantages of the invention will be apparent from the following description of the preferred embodiments thereof, and from the claims.

DESCRIPTION OF THE PREFERRED EMBODIMENTS

The steroid which is admixed with the drug is preferably a derivative of fusidic acid or cephalosporin $P_1$, preferably a derivative having formula (1), above.

These steroid molecules are all characterized in that they have the specific four-ring structure of fusidic acid and cephalosporin $P_1$, including the boat conformation of the B ring (in contrast to cholesterol derivatives such as bile salts, which have the B ring in the lower energy, more stable chair conformation).

Discussing the steroids of formula (1) in more detail, the steroid, at $C_{21}$, can be conjugated or unconjugated. The conjugating group can be any organic group which does not raise the critical micellar temperature of a 1% solution of the steroid above about 4° C. at pH 7.4 and does not raise the CMC above 4 mMolar at 37° C. in 0.15 M NaCl as measured by surface tension.

The conjugating group can be, e.g., any ionic function-containing straight or branch-chained amino acid. The amino acid can be aliphatic or aromatic, and can also be a homo- or a dihomo- amino acid, e.g. homotaurine or homoglycine, or an amphoteric amino acid, e.g., sulfobetaine or phosphobetaine. A straight or branched chain di- or tripeptide which terminates in an ionic function which is dissociated at pH 7.4 can also be employed. Peptides larger than tripeptides generally should not be used because they can unacceptably lower solubility. Any suitable uronic acid, e.g. glucuronic acid, can also be used.

Preferred conjugating amino acids are glycine and taurine. Preferred straight-chain peptides are diglycine and glutathione, and preferred branched chain peptides are sarcosylcysteine, hydroxyprolinetaurine, and sarcosyltaurine.

When the conjugating group is a polyether of at least sixteen carbon atoms, the group need not (although it can) contain an ionic function; the ionic function is unnecessary because such groups are highly polar and thus confer solubility without ionization. For smaller polyether groups, an ionic function is generally necessary, although it can be weakly ionizable since the smaller polyethers are polar themselves.

The group bonded to each of $C_6$ and $C_{16}$, independently, (W and E in formula (1)) can be OAc (OCOCH$_3$) as in naturally occurrig fusidic acid and cephalosporin $P_1$. Alternatively, E can be an alkyl (e.g., methyl or ethyl) or a different heteroalkyl (e.g. alkyloxy, alkylthio, or ether derivative) group of three or fewer carbon atoms; larger groups should not be used because they can unacceptably lower solubility. Group G, bonded to $C_3$, can be OH, as in naturally occurring fusidic acid and cephlosporin $P_1$. G can also be OAc, a lower alkyl group, or a different lower heteroalkyl group. Group W, if OAc, should be in the α-axial orientation; a β-axial orientation would render the molecule too polar.

The steroid should contain between zero and two, but no more than two, hydroxyl groups. These can be bonded only to $C_3$, $C_7$, $C_{11}$, and $C_{12}$.

The structure of the steroid molecule affects its chemical properties and thus its functioning as a drug transporting molecule. We believe that all of the steroid molecules used in the invention facilitate transport by self-associating to form reversed micelles within the membrane across which the drug is being transported; these reversed micelles, it is believed, function as pores, allowing the drug to pass through. A measure of the ability of a given steroid molecule's ability to form such reversed micelles is the hydrophobicity of the unconjugated form of the molecule, a property which can be quantified using the k' factor value, which is computed by observing the steroid's retention time in a high-performance liquid chromatography (HPLC) column under the conditions described above. As mentioned above, the k' factor value of the unconjugated derivative of the steroid should be at least 7 for the steroid to be suitable in the therapeutic compositions of the invention.

Critical micellar temperature (CMT) is an additional measure of a steroid's utility in the compositions of the invention. CMT is the temperature at which the steroid molecules abruptly become soluble and self-associate into micelles from the gel or crystalline state. This change is a reflection of the colligative properties of the system, and the micelles formed at a temperature just above the CMT can be small, e.g. dimers. The steroid molecules used in the invention should have a great enough tendency to self-associate to give a CMT of below 4° C., for a 1% aqueous solution, w/v, at pH 7.4.

The k' and CMT of the steroids used in the compositions of the invention are influenced by whether the steroid is conjugated at $C_{21}$ and, if so, by the nature of the conjugating group. Because the k' factor value is influenced by molecular size, unconjugated derivatives must be used in numerical comparisons involving steroids which are conjugated with different groups, or comparisons involving both conjugated and unconjugated steroids. Overall hydrophobicity and k' factor value generally decrease as the size of the conjugating group increases. However, such decrease is not a reflection of the hydrophobicity of the steroid nucleus. It is this hydrophobicity which is the important parameter for purposes of reversed micelle formation.

As has been mentioned, the k' factor value of the unconjugated derivative of any such steroid should be at least 7. (To give a few minimum k' values of conjugated steroids, the k' factor value of a glycine-conjugated steroid should be at least 3.4 to be useful in the invention. For a taurine-conjugated steroid, the k' factor value should be at least 1.)

It is desirable that conjugated steroids have strongly ionized conjugating groups which are capable of forming micelles at low concentrations (the critical micellar concentration, CMC, is a measure of this latter property). As mentioned above, examples of such desirable conjugating groups are taurine, homotaurine, sarcosyltaurine, and sulfobetaine. Steroids conjugated with such groups also have the advantages of stability and ease of synthesis.

Conjugation has additional effects as well, which provide the opportunity to tailor the conjugated steroid to a given clinical situation. For example, if the steroid is to be used to transport a drug across a mucosal membrane, e.g. the nasal mucosa, relatively long (e.g. homotaurine), branched (e.g. sarcosyltaurine), bulky (e.g. glucuronic acid), and amphoteric (e.g. sulfobetaine) groups are desirable, since they may cause the steroid to be held in the nasal membrane somewhat longer than unconjugated steroids conjugated with smaller conjugating groups.

Conjugation also, in some instances, lowers the CMC, so that only a small amount of steroid need be used, and also renders the steroid resistant to being taken out of solution by variations in pH, ionic strength, and by the presence of other ions (e.g. $C^{++}$) and other macromolecules. Conjugation further prevents retention by the body, promotes rapid excretion, and prevents hepatic metabolism to potentially toxic metabolites.

As mentioned above, conjugating groups are bonded to $C_{21}$ via any suitable linkage, e.g. amide or ester. Conjugation is carried out using conventional techniques, e.g. those described in U.S. Pat. No. 3,867,413, hereby incorporated by reference, and results in the conjugating group being bonded to $C_{21}$ via a suitable linkage. As an example, taurine bonded to $C_{21}$ via an amide linkage is shown below (the presence of a cation, e.g. $K^+$ or $Na^+$, is indicated in parentheses):

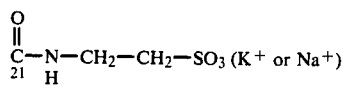

Some k' values of some unconjugated steroids useful in the invention are: cephalosporin $P_1$ (k'=9.5); fusidic acid (k'=20.7); 3-acetoxylfusidic acid (k'=26.4); and 24,25 dihydrofusidic acid (k'=27.1). In contrast, for example, the k' of helvolic acid is 4.7, the same as that of the bile salt ursodeoxycholic acid.

The properties of the steroid are also affected by the nature of the substituents at $C_3$, $C_6$ and $C_{16}$. Generally, OAc groups at these positions tend to aid solubility; however, OAc groups are also quite labile, and tend to decrease stability and shelf-life.

Any of the fusidic acid or cephalosporin $P_1$ derivatives are made by appropriately modifying commercially available fusidic acid or cephalosporin $P_1$. Such techniques are well known and are described, e.g., in U.S. Pat. No. 4,315,004, hereby incorporated by reference.

The drugs which are admixed with a steroid carrier preferably have a molecular weight of between about 100 daltons and 40,000 daltons. The drug is preferably water soluble or lipid soluble, and is preferably a peptide hormone such as insulin. Water soluble drugs, e.g. some peptides and vitamins, can be transported across mucosa membranes by any of the steroids of the invention, including those whose unconjugated derivatives have relatively low k' values (between about 7 and 15). For hydrophobic, lipid-soluble drugs, e.g. the lipid-soluble vitamins, the unconjugated derivative of the steroid should have a higher k' value, preferably above 20.

The peptide hormones such as insulin are some of the drugs for which the method of administration of the invention is most important. Other suitable peptide hormones are glucagon, parathyroid hormone, calcitonin, vasopressin, renin, prolactin, growth hormone, thyroid stimulating hormone, corticotrophin, follicle stimulating hormone, luteinising hormone, and chorionic gonadotrophin.

The invention can also be used to administer hormone releasing hormones, e.g. growth hormone releasing hormone, corticotrophic releasing hormone, luteinizing hormone, and growth hormone release inhibiting hormone (somatostatin).

Other suitable drugs include the physiologically active enzymes transfereses, hydrolases, isomerases, proteases, ligases, and oxidoreductases such as esterases, phosophatases, glycosidases and peptidases; enzyme inhibitors such as leupeptin, chymostatin and pepstatin; and growth factors such as tumor angiogenesis factor. Other suitable drugs are those normally absorbed to a limited extent across the gastrointestinal mucosa after oral administration; e.g. antihistamines, and drugs affecting the cardiovascular, renal, metabolic, hepatic and immune systems.

Many other drugs can also be administered according to the invention, e.g. the many drugs currently used to treat arthritis. Such drugs include narcotic pain relievers and anti-inflammatory agents.

Other suitable drugs are the water insoluble, fat-soluble hydrophobic drugs, e.g. steroids such as progesterone, estrogens and androgens and their analogs, and the that the dosage of insulin administered to the patient was 0.5 Units/kg body weight. As shown in Table I, below, five minutes after nasal administration the patient's serum insulin level had increased more than twenty-fold, demonstrating that the insulin had been rapidly and effectively absorbed through the nasal mucosa. Furthermore, as is shown in Table I, the patient's blood glucose was lowered significantly after twenty minutes, and more than halved after thirty minutes.

TABLE 1

| Time (minutes) | −20 | −10 | 0 | 5 | 10 | 15 | 20 | 25 | 30 | 40 | 50 | 60 | 75 | 90 |
|---|---|---|---|---|---|---|---|---|---|---|---|---|---|---|
| Blood Glucose mg/dl | 90 | 88 | 89 | | 82 | | 54 | | 32 | 38 | 50 | 72 | 85 | 89 |
| Serum Insulin µU/ml | 5.6 | | 4.5 | 115 | 100 | 95 | 62 | 30 | 22 | 10 | 6.4 | 8.8 | 5 | 3.5 | fat-soluble vitamins, e.g. vitamins A, D, E and K, and their analogs.

The surface across which transport occurs can be mucosal surfaces such as the nasal, buccal, rectal, intestinal (enteral), and vaginal mucosa or, in some circumstances, a skin surface such as the axilla, the gluteal cleft, between the toes, and the groin.

The ratio of drug and steroid present in a therapeutic composition will vary depending on a number of factors, including the k' and CMC of the steroid, the dosage of the drug to be administered, and the chemical characteristics, e.g. hydrophobicity, of the drug. Generally, the steroid is provided in an aqueous physiological buffer solution which is then mixed with the drug. The solution generally contains about 0.01% to 2.5%, w/v, steroid in, e.g. sodium phosphate buffered NaCl, pH 5-8, having NaCl concentration of about 0.05 M to about 0.6 M.

The concentration of the drug in the solution will of course vary widely, depending on the nature of the drug, and on the extent to which absorption is facilitated by the steroid. In some cases, administration according to the invention will cause a higher percentage of an administered dose to be delivered where needed than the conventional mode of administration; in other cases, a lower percentage will be delivered. Thus, generally, the amount of drug in a dose, according to the invention, will be between 0.1% and 1,000% the amount in a dose of the drug administered conventionally (where a conventional route exists).

The therapeutic composition can contain, in addition to steroid and drug, any other desired non-toxic, pharmaceutically acceptable substances, e.g. a preservative such as phenol or cresol.

The dosage given at any one time will depend on a number of factors including, in addition to those mentioned above, the frequency of administration.

The following specific example is intended to illustrate the invention, without acting as a limitation upon its scope.

EXAMPLE

Sodium tauro-24, 25-dihydrofusidic acid was dissolved in 0.15 M NaCl, pH 7.4 to form a 5% solution, w/v. Commercially available porcine regular insulin (U-500) (beef, human, or mixed insulin could have been used) was mixed in a total volume of 2.0 ml with 0.15 M NACl, pH 7.4, and the 5% solution of sodium tauro-24,25-dihydrofusidic acid to give final concentrations of 216 U/ml insulin and 1% (w/v) sodium tauro-24,25-dihydrofusidic acid. A normal human subject was administered, by nasal spray, two 75 microliter aliquots, so Other embodiments are within the following claims.
What is claimed is:

1. A composition useful for the treatment of diabetes comprising, in admixture:
   (a) as an active ingredient, a medically-effective amount of insulin; and
   (b) as an adjuvant, a biocompatible, water-soluble, amphiphilic steroid of the following formula:

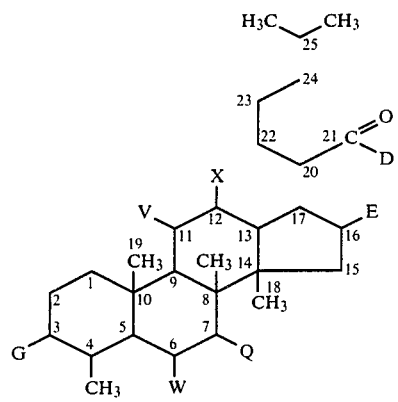

wherein a dashed line represents a single or a double bond;
   D represents a group having a molecular weight below 600 daltons which renders an effective amount of said steroid water-soluble at pH 7.4;
   E represents OAc, a lower alkyl group or a lower heteroalkyl group;
   G represents OAc, OH, a lower alkyl group or a lower heteroalkyl group;
   W represents OAc or H;
   Q represents OH or H, provided that, when W is OAc and Q is OH, Q is β-equatorial;
   V represents H or α-axial OH; and
   X represents H or α-axial OH, said steroid (i) containing two OH groups; and (ii) being capable of increasing the permeability to insulin of a body surface across which insulin is to be administered, in an amount effective to increase the permeability of said body surface to insulin.

2. The composition of claim 1 wherein the steroid is in unconjugated form, with D being selected from the group consisting of $O^-Na^+$, $O^-K^+$, $O^-Rb^+$ and $O^-Cs^+$.

3. The composition of claim 1 wherein D is a covalently linked organic group which contains at least two carbon atoms.

4. The composition of claim 3 wherein the covalently linked organic group is an amino acid containing an ionic function which is dissociated at pH 7.4.

5. The composition of claim 4 wherein the amion acid is selected from the group consisting of glycine, taurine, homoglycine and homotaurine.

6. The composition of claim 4 wherein the amino acid is selected from the group consisting of sulfobetaine and phosphobetaine.

7. The composition of claim 3 wherein the covalently linked organic group is a peptide of two to three amino acids, said peptide containing an ionic function which is dissociated at pH 7.4.

8. The composition of claim 7 wherein the peptide is selected from the group consisting of diglycine and glutathione.

9. The composition of claim 7 wherein the peptide is selected from the group consisting of sarcosylcysteine, hydroxyprolinetaurine, and sarcosyltaurine.

10. The composition of claim 3 wherein the covalently linked organic group is a heteroalkyl group of three or fewer carbon atoms, said group containing an ionic function which is dissociated at pH 7.4.

11. The composition of claim 3 wherein the covalently linked organic group is a uronic acid of six or fewer carbon atoms, said uronic acid containing an ionic function which is dissolved at pH 7.4.

12. The composition of claim 3 wherein the covalently linked organic group is a polyether containing between six and fourteen carbon atoms, inclusive, said polyether terminating in an ionic function which is dissociated at pH 7.4.

13. The composition of claim 3 wherein the covalently linked organic group is a polyether containing between sixteen and twenty-four carbon atoms, inclusive.

14. The composition of claim 3 wherein the covalently linked organic group is a polyether containing between sixteen and twenty-four carbon atoms, inclusive, said polyether terminating in an ionic function which is dissociated at pH 7.4.

15. The composition of claim 3 wherein the covalently linked organic group is bonded to $C_{21}$ of the steroid by an amide or an ester linkage.

16. The composition of claim 3 wherein the covalently linked organic group contains an ionic function, said ionic function being $SO_3^-$, $SO_4^-$, or $COO^-$.

17. The composition of claim 1 wherein the critical micellar temperature of an aqueous 1% solution, w/v, of said steroid is below 4° C. at pH 7.4.

18. The composition of claim 1 wherein the critical micellar concentration of said steroid is less than 4 mM in 0.15 M NaCl at 37° C., as measured by surface tension.

19. A composition useful for the treatment of diabetes comprising, in admixture:
 (a) as an active ingredient, a medically-effective amount of insulin; and
 (b) as an adjuvant, an ionized or partially ionized, water-soluble alkali salt of fusidic acid or a derivative thereof, said fusidic acid or derivative being capable of increasing the permeability to insulin of a body surface across which insulin is to be administered, in an amount effective to increase the permeability of said body surface to insulin.

20. A composition useful for the treatment of diabetes comprising, in admixture:
 (a) as an active ingredient, a medically-effective amount of insulin; and
 (b) as an adjuvant, an ionized or partially ionized, water-soluble alkali salt of cephalosporin $P_1$ or a derivative thereof, said cephalosporin or derivative being capable of increasing the permeability to insulin of a body surface across which insulin is to be administered, in an amount effective to increase the permeability of said body surface to insulin.

21. The composition of claim 19 wherein the derivative of fusidic acid is 24,25-dihydrofusidic acid.

22. The composition of claim 19 wherein the derivative of fusidic acid is 17,20-24,25-tetrahydrofusidic acid.

23. The composition of claim 19 wherein the derivative of fusidic acid is 3-acetoxyl-fusidic acid.

24. The composition of claim 19, 21, 22 or 23 wherein the fusidic acid or derivative thereof is conjugated at $C_{21}$.

25. The composition of claim 20 wherein the cephalosporin or derivative is conjugated at $C_{21}$.

26. The composition of claim 19 wherein the derivative of fusidic acid is tauro-24,25-dihydrofusidic acid.

27. The composition of claim 19 wherein the derivative of fusidic acid is tauro-17,20-24,25-tetrahydrofusidic acid.

28. A composition useful for the treatment of diabetes comprising, in admixture:
 (a) as an active ingredient, a medically-effective amount of insulin; and
 (b) as an adjuvant, sodium tauro-24,25-dihydrofusidic acid.

29. A method of administrating insulin for the treatment of diabetes which comprises applying to an animal body surface for absorption across said body surface a composition comprising, in admixture;
 (a) as an active ingredient, a medically-effective amount of insulin;
 (b) as an adjuvant, a biocompatible, water-soluble, amphiphilic steroid of the following formula:

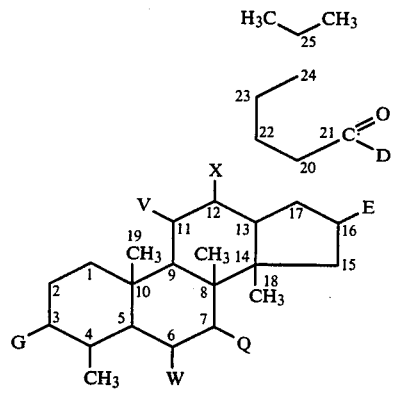

wherein a dashed line represents a single or a double bond;

D represents a group having a molecular weight below 600 daltons which renders an effective amount of said steroid water-soluble at pH 7.4;

E represents OAc, a lower alkyl group or a lower heteroalkyl group;

G represents OAc, OH, a lower alkyl group or a lower heteroalkyl group;

W represents OAc or H;

Q represents OH or H, provided that, when W is OAc and Q is OH, Q is β-equatorial;

V represents H or α-axial OH; and

X represents H or α-axial OH, said steroid (i) containing two OH groups; and (ii) being capable of increasing the permeability to insulin of a body surface across which insulin is to be administered, in an amount effective to increase the permeability of said body surface to insulin.

30. A method of administering insulin for the treatment of diabetes which comprises applying to an animal body surface for absorption across said body surface a composition comprising, in admixture:
    (a) as an active ingredient, a medically-effective amount of insulin;
    (b) as an adjuvant, an ionized or partially ionized, water-soluble alkali salt of fusidic acid or a derivative thereof, said fusidic acid or derivative being capable of increasing the permeability to insulin of a body surface across which insulin is to be administered, in an amount effective to increase the permeability of said body surface to insulin.

31. A method for administering insulin for the treatment of diabetes which comprises applying to an animal body surface for absorption across said body surface a composition comprising, in admixture:
    (a) as an acitve ingredient, a medically-effective amount of insulin; and
    (b) as an adjuvant, an ionized or partially ionized, water-soluble alkali salt of cephalosporin $P_1$ or a derivative thereof, said cephalosporin $P_1$ or derivative thereof being capable of increasing the permeability to insulin of a body surface across which insulin is to be administered, in an amount effective to increase the permeability of said body surface to insulin.

32. The method of claim 29, 30 or 31 wherein the animal body surface is a nasal mucosal surface.

33. A method of administering insulin for the treatment of diabetes which comprises applying to a nasal mucosal surface for absorption across said surface a composition comprising, in admixture:
    (a) a medically-effective amount of insulin; and
    (b) as an adjuvant, sodium tauro-24,25-dihydrofusidic acid.

* * * * *

UNITED STATES PATENT AND TRADEMARK OFFICE
CERTIFICATE OF CORRECTION

PATENT NO. : 4,548,922                    Page 1 of 2

DATED      : October 22, 1985

INVENTOR(S): Carey et al.                 Page 2

It is certified that error appears in the above-identified patent and that said Letters Patent is hereby corrected as shown below:

The formulae in Col. 8, claim 1 and claim 29 do not show the vertical dashed lines between carbons 24 and 25, and carbons 17 and 20. They should appear as follows:

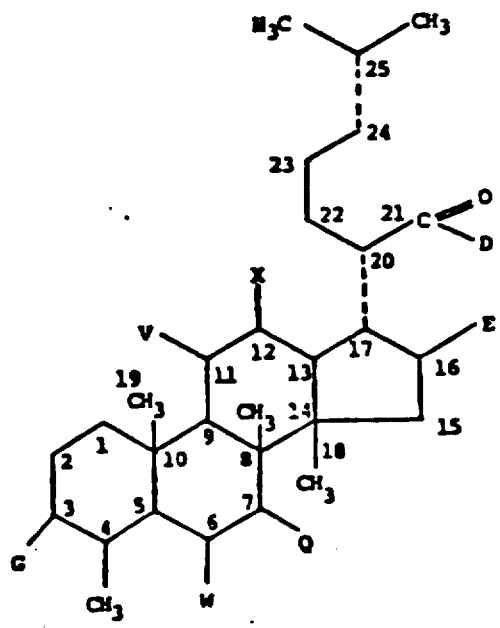

UNITED STATES PATENT AND TRADEMARK OFFICE
CERTIFICATE OF CORRECTION

PATENT NO. : 4,548,922

DATED : October 22, 1985

INVENTOR(S) : Carey et al.

It is certified that error appears in the above-identified patent and that said Letters Patent is hereby corrected as shown below:

Col. 2, line 51, "-$Cs^{30}$" should read -- -$Cs^{+}$ --;

Col. 4, line 41, "occurrig" should read --occurring--;

Col. 5, line 58, "unconjugated steroids conjugated" should read --unconjugated steroids or steroids conjugated--;

Col. 5, line 64, "(e.g. $C^{++}$)" should read --(e.g. $Ca^{++}$)--;

Col. 6, line 58, "luteinizing hormone and growth" should read --luteinizing hormone releasing hormone, and growth--;

Col. 7, line 33, "having NaCl" should read --having an NaCl--;

Col. 9, line 4, "amion" should read --amino--;

Col. 9, line 28, "dissolved" should read --dissociated--;

Col. 12, line 1, "method for" should read --method of--;

Signed and Sealed this

Twenty-fourth Day of December 1985

[SEAL]

Attest:

DONALD J. QUIGG

Attesting Officer

Commissioner of Patents and Trademarks